United States Patent [19]

Knops et al.

[11] 4,255,437
[45] Mar. 10, 1981

[54] COMBATING FUNGI WITH 2-ARYL-5-ALKYL-3,4-DIOXO-1,2,5-THIAZOLIDINE-1-OXIDES

[75] Inventors: Hans-Joachim Knops, Wuppertal; Wilhelm Brandes, Leichlingen; Volker Paül, Solingen, all of Fed. Rep. of Germany

[73] Assignee: Bayer Aktiengesellschaft, Leverkusen, Fed. Rep. of Germany

[21] Appl. No.: 95,716

[22] Filed: Nov. 19, 1979

[30] Foreign Application Priority Data

Dec. 7, 1978 [DE] Fed. Rep. of Germany ....... 2852869

[51] Int. Cl.$^3$ .................... A01N 43/82; C07D 285/10
[52] U.S. Cl. ..................................... 424/270; 548/135
[58] Field of Search ......................... 548/135; 424/270

[56] References Cited

U.S. PATENT DOCUMENTS 4,094,986  6/1978  Rokach et al. ..................... 548/135

OTHER PUBLICATIONS

Neidlein et al., "Synthesis", (1977), No. 1, Jan., pp. 63–64.
Neidlein et al., "Chem. Ber.," 110(9), 1977, pp. 3149–3160.

Primary Examiner—Anton H. Sutto
Attorney, Agent, or Firm—Sprung, Felfe, Horn, Lynch & Kramer

[57] ABSTRACT

2-Aryl-5-alkyl-3,4-dioxo-1,2,5-thiadiazolidine-1-oxide of the formula

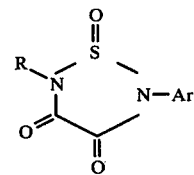

in which
Ar is optionally substituted aryl and
R is alkyl,
which possess fungicidal properties.

8 Claims, No Drawings

COMBATING FUNGI WITH 2-ARYL-5-ALKYL-3,4-DIOXO-1,2,5-THIAZOLIDINE-1-OXIDES

The present invention relates to and has for its objects the provision of particular new 2-aryl-5-alkyl-3,4-dioxo-1,2,5-thiadiazolidine-1-oxides which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that certain thiuram disulphides, for example tetramethyl-thiuram disulphide, exhibit good fungicidal properties (see U.S. Pat. No. 1,972,961). It is also known that zinc ethylene-1,2-bis-dithiocarbamate is a good agent for combating fungal diseases of plants (see Phytopathology 33, 1113 (1963)). The action of both categories of compound is however not always fully satisfactory in certain areas of indication, especially if small amounts and low concentrations are used.

The present invention now provides, as new compounds, the 3,4-dioxo-1,2,5-thiadiazolidine-1-oxides of the general formula

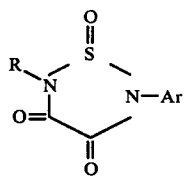

(I)

in which
Ar represents optionally substituted aryl and
R represents alkyl.

Surprisingly, the 3,4-dioxo-1,2,5-thiadiazolidine-1-oxides according to the invention exhibit a substantially higher fungicidal action, especially against species of Botrytis, than the compounds tetramethyl-thiuram disulphide and zinc ethylene-1,2-bis-dithiocarbamate, known from the prior art, which are recognized as good agents of the same type of action. The active compounds according to the invention thus represent an enrichment of the art.

Preferably, in formula (I),
Ar represents phenyl which optionally carries one or more substituents selected independently from halogen, alkyl with 1 or 2 carbon atoms and halogenoalkyl with up to 2 carbon atoms and up to 3 identical or different halogen atoms (preferred halogen atoms being fluorine and chlorine), and R represents straight-chain or branched alkyl with 1 to 6 carbon atoms.

Very particularly preferred compounds of the formula (I) are those in which
Ar represents phenyl which is monosubstituted or disubstituted by chlorine, bromine, methyl or trifluoromethyl, the substituents, in the case of disubstitution, being identical or different, and
R represents methyl, ethyl, n-propyl, iso-propyl isobutyl, sec.-butyl or tert.-butyl.

Specifically, in addition to the compounds mentioned later in the preparative examples, the following compounds of the general formula (I) may be mentioned:

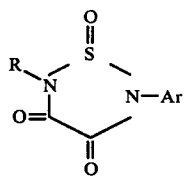

(I)

| R | Ar | R | Ar |
|---|----|---|----|
| $CH_3$ | 2,4-Cl,Cl-phenyl | $C_2H_5$ | 2,4-Cl,Cl-phenyl |
| $i\text{-}C_3H_7$ | 2,4-Cl,Cl-phenyl | $CH_3$ | 2,4-Cl,Cl-phenyl |
| $i\text{-}C_3H_7$ | 4-Cl-phenyl | $CH_3$ | 4-Cl-phenyl |
| $i\text{-}C_3H_7$ | 2,4-Cl,Cl-phenyl | $CH_3$ | 2,4-Cl,Cl-phenyl |
| $i\text{-}C_3H_7$ | $CF_3$-phenyl | $CH_3$ | $CF_3$-phenyl |
| $C_2H_5$ | Cl-phenyl | $C_2H_5$ | 2,4-Cl,Cl-phenyl |
| $C_2H_5$ | 4-Cl-phenyl | $C_2H_5$ | $CF_3$-phenyl |

The invention also provides a process for the preparation of a 3,4-dioxo-1,2,5-thiadiazolidine-1-oxide of the formula (I) in which a substituted sulphur-diimide of the general formula R—N=S=N—Ar (II), in which
Ar and R have the above-mentioned meanings, is reacted with oxalyl chloride which has the formula

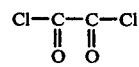

(III), in the presence of an organic diluent, and the 1,1-dichloro-3,4-dioxo-1,2,5-thiadiazolidine thereby produced, of the general formula

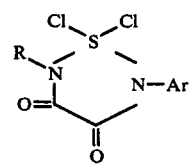

(IV), in which

Ar and R have the above-mentioned meanings, is hydrolyzed, without isolation, to give the corresponding 3,4-dioxo-1,2,5-thiadiazolidine-1-oxide.

If, for example, N-tert.-butyl-N'-3,5-dichlorophenyl-sulphur-diimide and oxalyl chloride are used as starting materials, the course of the reaction in the process according to the invention can be represented by the following equation:

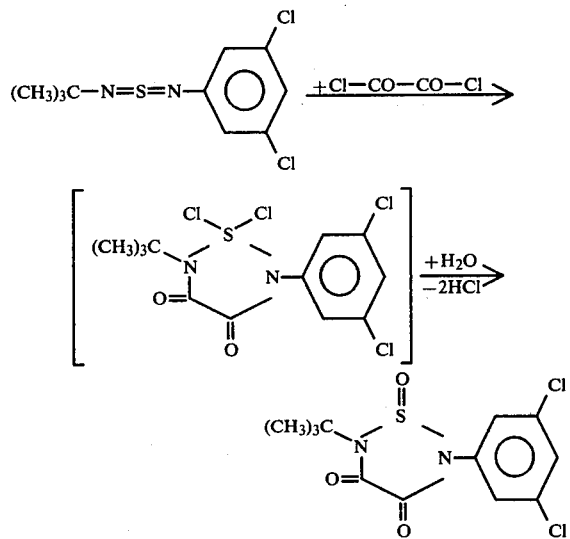

The formula (II) provides a general definition of the substituted sulphur-diimides required as starting materials in carrying out the process according to the invention. In this formula, Ar and R preferably have those meanings which have already been mentioned as preferred in connection with formula (I).

Substituted sulphur-diimides of the formula (II) are known (see Synthesis 1977, 63) and can be prepared by a process wherein aliphatic sulphur-diimides of the general formula

in which

R has the above-mentioned meaning, are reacted with isocyanates of the general formula

in which

Ar has the above-mentioned meaning, in the presence of an inert organic solvent, for example toluene, at temperatures between 20° and 80° C. (see in this context also the information in Tetrahedron Letters 1965, 1491; Chemische Berichte 111, 3460 (1978); and in the preparative examples later in this text). The substituted sulphur-diimides of the formula (II) thus obtained, can be reacted, in accordance with the invention, either directly or after isolation.

Aliphatic sulphur-diimides of the formula (V) are known (see the above-mentioned literature references as well as Chemische Berichte 103, 2152 (1970) and the literature references cited therein); they can all be obtained in accordance with the processes described in the literature by reacting sulphur tetrahalides, for example sulphur tetrachloride, with appropriate alkylamines at low temperatures or by treating a mixture of the primary amine mentioned and its mono-N-halogen compound, especially its mon-N-chlorine compound or mono-N-bromine compound, with bis-(dimethylamino)sulphane in chloroform at temperatures between −30° and +10° C.

The isocyanates of the formula (VI) are generally known compounds of organic chemistry.

Oxalyl chloride, additionally to be used as a starting material for the process according to the invention, is defined by the formula (III). Oxalyl chloride is a generally known compound of organic chemistry.

Preferred diluents for the reaction according to the invention are inert organic solvents. These include, as preferences, aromatic hydrocarbons (which may be halogenated), for example benzene, toluene, xylene or 1,2-dichlorobenzene, and aliphatic halogenated hydrocarbons, for example methylene chloride, chloroform or carbon tetrachloride.

In the reaction according to the invention, the reaction temperatures can be varied within a substantial range. In general, the reaction is carried out at from 0° to 100° C., preferably from 20° to 60° C.

In carrying out the reaction according to the invention, equimolar amounts of the reactants are preferably used. The 1,1-dichloro-3,4-dioxo-1,2,5-thiadiazolidines of the formula (IV), which arise as intermediate products, are directly reacted further, without isolation. The hydrolysis of the compounds (IV) may be effected in the usual manner. The isolation of the compounds of the formula (I) is carried out in accordance with customary methods.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Botrytis species, such as the gray mold causative organism (*Botrytis cinerea*).

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dipersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, especially 0.01 to 10 g, are generally employed per kilogram of seed.

For the treatment of soil, active compound concentrations of 0.00001 to 0.1% by weight, especially 0.0001 to 0.02%, are required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

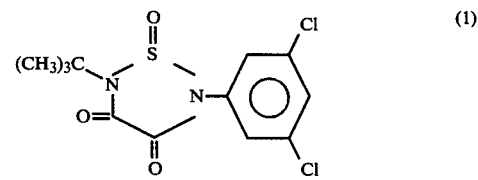

(1)

6.3 g (0.05 mol) of oxalyl chloride in 50 ml of carbon tetrachloride were added dropwise, while stirring, to 13.1 g (0.05 mol) of N-3,5-dichlorophenyl-N'-tert.-butylsulphur diimide in 200 ml of carbon tetrachloride. Stirring was continued for 30 minutes with exclusion of moisture, 20 ml of water were added and the mixture was stirred for a further 2 hours. The product which had precipitated was filtered off, washed with water and heated, in 300 ml of toluene, for 3 hours under a water separator. The crystals which precipitated after cooling were filtered off and dried. 12 g (72% of theory) of 2-(3,5-dichlorophenyl)-5-tert.-butyl-3,4-dioxo-1,2,5-thiadiazolidine-1-oxide of melting point 182° C. were obtained.

EXAMPLE 2

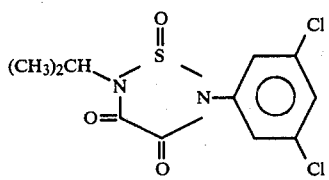
(2)

N-Isopropyl-N'-3,5-dichlorophenyl-sulphur-diimide was was prepared from diisopropyl-sulphur-diimide and 3,5-dichlorophenyl isocyanate and was subsequently reacted, without isolation, with oxalyl chloride.

30 g (0.2 mol) of diisopropyl-sulphur-diimide were added, dropwise, at room temperature, to a solution of 37 g (0.2 mol) of 3,5-dichlorophenyl isocyanate in 400 ml of toluene. The reaction temperature was kept at between 40° C. and 50° C. Stirring was then continued until the reaction temperature had been reached, the mixture was concentrated and the residue was taken up in 500 ml of absolute carbon tetrachloride. 25 g (0.2 mol) of oxalyl chloride were then added dropwise at such a rate that the reaction temperature did not rise above 40° C. One hour after completion of the addition, 20 ml of water were added to the reaction mixture and the batch was stirred until the evolution of hydrogen chloride has subsided. The mixture was then concentrated, the residue was extracted by boiling with petroleum ether, and the crystals which had precipitated were filtered off. 20 g (32% of theory) of 2-(3,5-dichlorophenyl)-5-isopropyl-3,4-dioxo-1,2,5-thiadiazolidine-1-oxide of melting point 109° C. were obtained.

The following compounds of the general formula

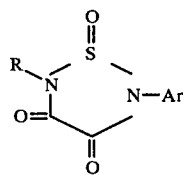
(I)

were obtained analogously:

| Compound No. | Ar | R | Melting point (°C.) |
|---|---|---|---|
| 3 | 3,5-Cl₂-C₆H₃ | n-C₃H₇ | 126–28 |
| 4 | 3-CF₃-C₆H₄ | C(CH₃)₃ | 131–33 |
| 5 | 3-Cl-C₆H₄ | C(CH₃)₃ | 112–15 |
| 6 | 3,4-Cl₂-C₆H₃ | C(CH₃)₃ | 155 |
| 7 | 3-Cl-C₆H₄ | C(CH₃)₃ | 113 |
| 8 | 2,5-Cl₂-C₆H₃ | C₂H₅ | 95–110 |

The fungicidal activity of the compounds of this invention is illustrated by the following examples wherein the compounds according to the present invention are each identified by the number (given in brackets) from preparative Examples 1 and 2.

EXAMPLE 3

Botrytis test (beans)/protective
Solvent: 4.7 parts by weight of acetone
Dispersing agent: 0.3 part by weight of alkylaryl polyglycol ether
Water: 95.0 parts by weight The amount of active compound required for the desired concentration of active compound in the spray liquor was mixed with the stated amount of the solvent and the concentrate was diluted with the stated amount of water which contained the stated amount of the dispersing agent.

Plants of *Phaseolus vulgaris* in the 2-leaf stage were sprayed with the spray liquor until dripping wet. After 24 hours, 2 small pieces of agar on which *Botrytis cinerea* had been grown were placed on each leaf. The inoculated plants were set up in a darkened, moist chamber at 20° C. 3 days after the inoculation, the size of the infection spots on the leaves was rated.

The ratings obtained were converted to percent infection. 0% meant no infection and 100% meant that the infection spot had developed completely, In this test, for example, the following compounds showed a very good action which was superior to that of the compounds known from the prior art: (2) and (3).

EXAMPLE 4

Mycelium growth test
Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate
Ratio of solvent mixture to nutrient medium:
2 parts by weight of solvent mixture
100 parts by weight of agar nutrient medium
Composition of the solvent mixture:
0.19 part by weight of acetone or dimethylformamide
0.01 part by weight of emulsifier (alkylaryl polyglycol ether)
1.80 parts by weight of water The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg.C) and was then poured into Petri dishes of 9 cm diameter. Control plates to which the preparation had not been added were also set up.

When the nutrient medium had cooled and solidified, the plates were inoculated with the species of organisms stated hereinbelow and incubated at about 21 deg.C.

Evaluation was carried out after 4–10 days, dependent upon the speed of growth of the organisms. When evaluation was carried out the radial growth of the organism on the treated nutrient media was compared with the growth on the control nutrient medium. In the evaluation of the organism growth, the following characteristic values were used:

1 no growth
up to 3 very strong inhibition to growth
up to 5 medium inhibition of growth
up to 7 slight inhibition of growth
9 growth equal to that of untreated control.

In this test, for example, the following compounds showed a very good action which was superior to that of the compounds known from the prior art: (2) and (3).

The micro-organisms used in the above test were the fungi: Sclerotinia sclerotiorum, Fusarium nivale, Rhizoctonia solani, Cochliobolus miyabeanus, Botrytis cinerea, Pyriculariae oryzae.

It will be appreciated that the instant specification and examples are set forth by way of illustration and not limitation, and that various modifications and changes may be made without departing from the spirit and scope of the present invention.

What we claim is:

1. A 2-aryl-5-alkyl-3,4-dioxo-1,2,5-thiadiazolidine-1-oxide of the formula

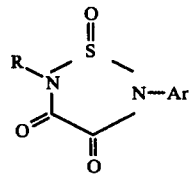

in which
Ar is phenyl substituted with at least one of halogen, methyl, ethyl, halogenomethyl or halogenoethyl, and
R is alkyl with 1 to 6 carbon atoms.
2. A compound according to claim 1, in which Ar is 3,5-dichlorophenyl.

3. A compound according to claim 1, in which said compound is 2-(3,5-dichlorophenyl)-5-tert.-butyl-3,4-dioxo-1,2,5-thiazolidine-1-oxide of the formula

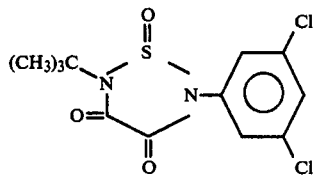

4. A compound according to claim 1, in which said compound is 2-(3,5-dichlorophenyl)-5-isopropyl-3,4-dioxo-1,2,5-thiazolidine-1-oxide of the formula

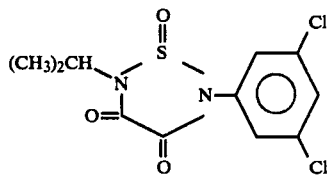

5. A compound according to claim 1, in which said compound is 2-(3,5-dichlorophenyl)-5-n-propyl-3,4-dioxo-1,2,5-thiazolidine-1-oxide of the formula

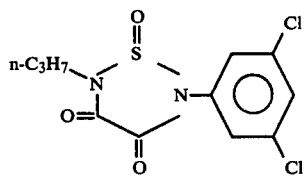

6. A fungicidal composition containing as active ingredient a fungicidally effective amount of a compound according to claim 1 in admixture with a diluent.
7. A method of combaitng fungi, which comprises applying to the fungi, or to a habitat thereof, a fungicidally effective amount of a compound according to claim 1.
8. The method according to claim 7, in which the compound is
2-(3,5-dichlorophenyl)-5-tert.-butyl-3,4-dioxo-1,2,5-thiazolidine-1-oxide,
2-(3,5-dichlorophenyl)-5-isopropyl-3,4-dioxo-1,2,5-thiazolidine-1-oxide, or
2-(3,5-dichlorophenyl)-5-n-propyl-3,4-dioxo-1,2,5-thiazolidine-1-oxide.

* * * * *